United States Patent [19]

Iwahi et al.

[11] Patent Number: 5,013,743
[45] Date of Patent: May 7, 1991

[54] SELECTIVE ANTIBACTERIAL AGENT AGAINST CAMPYTOBACTER

[75] Inventors: Tomoyuki Iwahi; Hiroshi Satoh, both of Suita, Japan

[73] Assignee: Takeda Chemical Industries, Ltd., Osaka, Japan

[21] Appl. No.: 478,405

[22] Filed: Feb. 12, 1990

[30] Foreign Application Priority Data

Feb. 10, 1989 [JP] Japan .................................. 1-032374
Sep. 15, 1989 [JP] Japan .................................. 1-239233

[51] Int. Cl.$^5$ ............................................ A01N 43/40
[52] U.S. Cl. ..................................... 514/338; 514/322; 514/925
[58] Field of Search ........................ 514/322, 925, 338

[56] References Cited

FOREIGN PATENT DOCUMENTS 0174726  3/1986  European Pat. Off. ............ 514/322

OTHER PUBLICATIONS

PCT Gazette—Section I, No. 20/1990, p. 5845, abstract of WO90/09175, Published 23 Aug. 1990.
Sassoon Levi et al., "*Campylobacter pylori*, Gastrin, and Duodenal Ulcer", The Lancet, Aug. 12, 1989, pp. 389–390.
Barry J. Marshall et al., "Antibacterial Action of Bismuth in Relation to *Campylobacter pyloridis* Colonization and Gastritis" Digestion, vol. 37, Supp. 2, (1987) pp. 16–30.
George E. Buck et al., "Relation of *Campylobacter pyloridis* to Gastritis and Peptic Ulcer", The Journal of Infectious Diseases, vol. 153, No. 4, (Apr. 1986) pp. 664–669.
Sassoon Levi et al., "*Campylobacter pylori* and Duodenal Ulcers: The Gastrin Link", The Lancet, May 27, 1989, pp. 1167–1168.
C. Stewart Goodwin et al., "The Minimum Inhibitory and Bactericidal Concentrations of Antibiotics and Anti-Ulcer Agents against *Campylobacter pyloridis*", Journal of Antimicrobial Chemotherapy, vol. 17, (1986) pp. 309–314.

Primary Examiner—Stanley J. Friedman
Assistant Examiner—Greg Hook
Attorney, Agent, or Firm—Wegner, Cantor, Mueller & Player

[57] ABSTRACT

The compound represented by the formula;

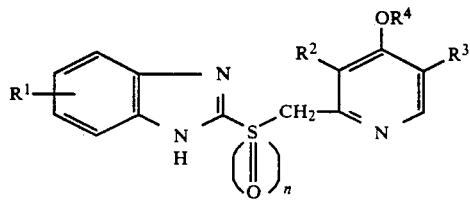

[wherein $R^1$ stands for hydrogen, methoxy or trifluoromethyl; $R^2$ and $R^3$, being the same or different from each other, stand for hydrogen or methyl; $R^4$ stands for optionally substituted hydrocarbon residue; and n denotes 0 or 1] or a salt thereof show excellent antibacterial activities, against the genus Campylobacter, especially against *Campylobacter pylori*, and they are used for preventing or treating infectious diseases caused by the said bacteria.

15 Claims, No Drawings

SELECTIVE ANTIBACTERIAL AGENT AGAINST CAMPYTOBACTER

FIELD OF THE INVENTION

This invention relates to a pharmaceutical composition containing pyridine derivatives, known as a compound having anti-ulcer activity, useful as antibacterial agent and a method for preventing or treating infectious diseases caused by the genus Campylobacter by administering the pyridine derivatives.

BACKGROUND OF THE INVENTION

Bacteria belonging to the genus Campylobacter have been known as possible causes of gastro-intestinal disorders of animals For example, *Campylobacter pylori* is isolated with high frequency from the gastic mucosa of patients suffering from gastritis and peptic ulcer, and, several investigators have suggested that this organism might participate in the pathogenesis of these diseases. (cf: The Journal of Infectious Desease, Vol. 153, pp. 664-669, 1986 and The Lancet, May 27, pp. 1167-1168, 1989). Furthermore, the close association between the presence of *Campylobacter pylori* and duodenal ulcers has been also suggested (cf: Digestion, Vol. 37, pp. 16-30, 1987).

Until now some studies dealing with the effectiveness of antibiotics, bismuth citrate, anti-ulcer agent (cimetidine, ranitidine, etc.) or related compounds in the treatment of the infectious diseases associated with the genus Campylobacter have been reported. (cf: Journal of Antimicrobial Chemotherapy, Vol. 17, pp. 309-314, 1986), but no practical use for them has been realized yet.

As mentioned above, no clinically effective pharmaceutical agents against bacterial infections due to the genus Campylobacter have been brought into existence. The present invention provides an antibacterial agent effective to the genus Campylobacter.

SUMMARY OF THE INVENTION

The present invention relates to:
1. An antibacterial composition which contains an effective amount of a compound of the formula (I);

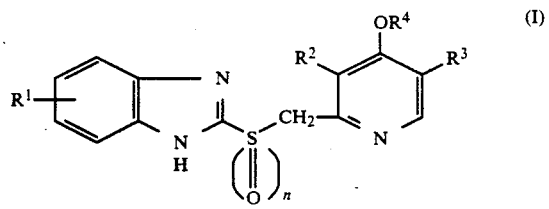

wherein $R^1$ stands for hydrogen, methoxy or triflouromethyl; $R^2$ and $R^3$, being the same or different from each other, stand for hydrogen or methyl; and $R^4$ stands for an optionally substituted hydrocarbon residue and n denotes 0 or 1, or a pharmacologically acceptable salt thereof, and pharmaceutically acceptable carriers.

2. A method for preventing or treating infectious diseases caused by the genus Campylobacter, which comprises administering a compound of the formula (I) or a pharmacologically acceptable salt thereof.

DETAILED DESCRIPTION OF THE INVENTION

The composition according to the present invention shows excellent antibacterial activities, against the genus campylobacter, especially against *Campylobacter pylori*, and they are used for preventing or treating infectious diseases caused by the said bacteria.

In the compound (I), preferable examples of the hydrocarbon residue in the optionally substituted hydrocarbon shown by $R^4$ include 1-6 C straight-chain or branched alkyl groups, 2-6 C alkenyl groups and alkynyl groups; the alkyl groups are exemplified by methyl, ethyl, propyl, isopropyl, butyl, 1-methylpropyl, 2-methylpropyl, t-butyl, pentyl, 2-methylbutyl, hexyl, 4-methylpentyl, etc.; the alkenyl groups are exemplified by vinyl, 2-propenyl, 2-butenyl, 3-butenyl, 2-methyl-2-propenyl, 2-pentenyl, 3-pentenyl, 4-pentenyl, 2-methyl-2-butenyl, 3-methyl-2-butenyl, 2-hexenyl, 3-hexenyl, 4-hexenyl, 5-hexenyl, 3-methyl-2-pentenyl, 4-methyl-3-pentenyl, etc.; the alkynyl groups are exemplified by ethinyl, 2-propinyl, 1-methyl-2-propinyl, 2-butynyl, 3-butynyl, 1-methyl-2-butynyl, 2-pentynyl, 3-pentynyl, 4-pentynyl, 2-methyl-3-pentynyl, 2-hexynyl, etc. As the substituents, mention is made of fluorine and 1-3 C alkoxy groups. The number of substituents ranges from 1 to 9, in the case of fluorine, and the number is 1 or 2, in the case of alkoxy groups. Examples of thus substituted compounds include 2,2,2-trifluoroethyl, 2,2,3,3,3-pentafluoropropyl, 2,2,3,3-tetrafluoropropyl, 1,1,1,3,3,3-hexafluoro-2-propyl, 2,2,3,3,4,4,4-heptafluorobutyl, 2,2,3,3,4,4-hexafluorobutyl, 2,2,3,3,4,4,5,5-octaflouropentyl, 2,2,3,3,4,4,5,5,5-nonafluoropentyl, cis-2-fluoro-2-butenyl, 2,2,3,4,4-pentafluoro-3-butenyl, 1,1,1-trifluoro-3-pentyn-2-yl, methoxymethyl, ethoxymethyl, propoxyethyl, 2-methoxypropyl, 3-methoxypropyl, 3-ethoxypropyl, 4-methoxybutyl, trans-3-methoxy-2-propenyl, trans-3-methoxy-2-butenyl, 4-methoxy-2-butynyl, 4methoxy-2-butynyl, etc. Among these, fluorinated 2-6 C straight-chain or branched alkyl groups are especially preferable.

The compound (I) can be produced by a known method, for example, the method disclosed in European Patent No. 174726, and methods disclosed in the laid-open official gazette of European Patent No. 268956 and in the laid-open official gazette of British patent No. 2134523, or methods analogous thereto.

Salts of the compound (I) are exemplified by pharmaceutically acceptable ones obtained by a known method (laid-open official gazette of European Patent No. 124495) or methods analogous thereto, such as salts of alkali metal or alkaline earth metal, e.g. sodium, potassium, calcium, magnesium, etc.

The compound (I) shows antibacterial action against the genus Campylobacter, for example, *Campylobacter pylori*.

In the following, the antibacterial action of the compound (I) is described by way of Experimental Examples.

EXPERIMENTAL EXAMPLE 1

The minimum inhibitory concentration (MIC) of each compound was determined by the agar-plate dilution method based on the standard method advocated by Japan Society of Chemotherapy [cf: Chemotherapy, Jan. '81, p. 76]. The volume of agar medium per plate was 20 ml. The compounds tested are shown in Table 1.

TABLE 1

| Compound No. | $R^1$ | $R^2$ | $R^3$ | $R^4$ | n |
|---|---|---|---|---|---|
| 1 | H | $CH_3$ | H | $CH_2CF_3$ | 1 |
| 2 | 5-$OCH_3$ | $CH_3$ | $CH_3$ | $CH_3$ | 1 |
| 3 | H | $CH_3$ | H | $CH_2CF_2CF_3$ | 1 |
| 4 | H | $CH_3$ | H | $CH_2CF_2CF_2H$ | 1 |
| 5 | H | $CH_3$ | H | $CH_2(CF_2)_2CF_2H$ | 1 |
| 6 | H | $CH_3$ | H | $CH_2CF_3$ | 0 |
| 7 | H | H | H | iso-butyl | 0 |
| 8 | 5-$CF_3$ | H | H | iso-butyl | 0 |
| 9 | 5-$CF_3$ | H | H | iso-propyl | 0 |
| 10 | 5-$CF_3$ | H | H | $CH_2CH=CH_2$ | 0 |
| 11 | 5-$CF_3$ | H | H | $CH_2C\equiv CH$ | 0 |
| 12 | H | $CH_3$ | H | $CH_2CF_2CF_2H$ | 0 |
| 13 | H | $CH_3$ | H | $CH_2CF_2CF_3$ | 0 |
| 14 | H | $CH_3$ | H | $CH_2(CF_2)_2CF_2H$ | 0 |

Each of the test compounds was dissolved in dimethylsulfoxide at a concentration of 80 mg/ml or 40 mg/ml, and diluted 10 times with sterile distilled water. Furthermore, the aqueous solution of 8 mg/ml or 4 mg/ml was diluted serially 2-fold with sterile distilled water. To 2 ml of the diluted solution was added 18 ml of Brucella agar (BBL Microbiology Systems, Becton Dickinson and Co., Cockeysville, Md. 21030) containing 7% defibrinated horse blood (manufactured by Nippon Bio-supp. Center) and mixed well.

Test strains frozen at −80° C. in Brucella broth (BBL) containing 10% horse serum were thawed and inoculated on a Brucella agar slant medium containing 7% defibrinated horse blood. The medium was incubated anaerobically at 37° C. for 3 days in a jar containing a piece of sponge sufficiently impregnated with water and Campy Pak ™ (BBL).

The organisms grown on the slant medium were collected and suspended in a Brucella broth to correspond to the turbidity of about $10^8$ CFU/ml of common bacteria. One platinum loop of inoculum was streaked on the medium plates for determination. The plates were incubated under the same conditions as described above. After three-day incubation, the growth of bacteria was observed with naked eyes, and MIC (unit:μg/ml) was determined. The results are shown in Table 2 and Table 3.

TABLE 2

| Compound | A | B | C | D | E | F | G |
|---|---|---|---|---|---|---|---|
| 1 | 12.5 | 6.25 | 6.25 | 6.25 | 6.25 | 6.25 | 3.13 |
| 2 | 25 | 25 | 12.5 | 12.5 | 25 | 25 | 12.5 |
| 3 | 3.13 | 6.25 | 3.13 | 3.13 | 3.13 | 1.56 | 6.25 |
| 4 | 1.56 | 6.25 | 6.25 | 1.56 | 1.56 | 0.78 | 6.25 |
| 5 | 1.56 | 3.13 | 1.56 | 1.56 | 1.56 | 1.56 | 6.25 |

*Test strains

TABLE 3

| Compound | A | B | C | D | E | F | G |
|---|---|---|---|---|---|---|---|
| 6 | 6.25 | 12.5 | 6.25 | 3.13 | 12.5 | 25 | 6.25 |
| 7 | 12.5 | 12.5 | 12.5 | 12.5 | 12.5 | 12.5 | 12.5 |
| 8 | 12.5 | 12.5 | 12.5 | 12.5 | 12.5 | 12.5 | 12.5 |
| 9 | 12.5 | 12.5 | 12.5 | 12.5 | 12.5 | 12.5 | 12.5 |
| 10 | 25 | 25 | 25 | 25 | 25 | 25 | 25 |
| 11 | 12.5 | 12.5 | 12.5 | 12.5 | 12.5 | 12.5 | 12.5 |
| 12 | 1.56 | 0.78 | 1.56 | 1.56 | 1.56 | 1.56 | 0.78 |
| 13 | 1.56 | 1.56 | 1.56 | 1.56 | 1.56 | 1.56 | 1.56 |
| 14 | 3.13 | 3.13 | 3.13 | 1.56 | 1.56 | 3.13 | 1.56 |

*Test strains
A: *C. pylori* NCTC 11916
B: *C. pylori* NCTC 11637
C: *C. pylori* PCL 56
D: *C. pylori* CPY 0011-1
E: *C. pylori* KS 13
F: *C. pylori* CLO 1
G: *C. pylori* CLO 6

As is clear from Table 2 and Table 3, compounds 1 to 14 respectively showed antibacterial activities against the genus Campylobacter. And, the derivatives [$R^4$ of the Compound (I) is a fluorinated alkyl group] (compounds 1, 3, 4, 5, 6, 12, 13 and 14) showed stronger antibacterial activity when compared with other derivatives.

EXPERIMENTAL EXAMPLE 2

Antibacterial activities of some compounds of the present invention against aerobic common bacteria were examined.

MICs (unit: μg/ml) of the test compounds, i.e. compounds 1, 2 and 6 employed in Experimental Example 1, were determined by the standard agar-plate dilution method of Japan Society of Chemotherapy. The results are shown in Table 4.

TABLE 4

| Test strains | | Compound 1 | Compound 2 | Compound 6 |
|---|---|---|---|---|
| S. aureus | FDA 209P | >400 | >400 | >400 |
| S. aureus | 308 A-1 | >400 | >400 | >400 |
| S. aureus | 1840 | >400 | >400 | >400 |
| S. aureus | N-241 | >400 | >400 | >400 |
| S. aureus | J-108 | >400 | >400 | >400 |
| S. aureus | P 114 | >400 | >400 | >400 |
| S. aureus | C 260 | >400 | >400 | >400 |
| S. pyogenes | E-14 | >400 | >400 | >400 |
| S. pyogenes | S-8 | >400 | >400 | >400 |
| S. mitis | America | >400 | >400 | >400 |
| S. faecium | IFO 3128 | >400 | >400 | >400 |
| S. pneumoniae | Type 1 | >400 | >400 | >400 |
| C. diphtheriae | Tront | >400 | >400 | >400 |
| E. coli | NIHJ JC-2 | >400 | >400 | >400 |
| E. coli | 0-111 | >400 | >400 | 40o |
| E. coli | T 7 | >400 | 40D | >400 |
| C. freundii | IFO 12681 | >400 | >400 | >400 |
| C. freundii | TN 474 | >400 | >400 | >400 |
| K. pneumoniae | DT | >400 | >400 | >400 |
| K. oxytoca | TN 1711 | >400 | >400 | >400 |
| E. cloacae | IFO 12937 | >400 | >400 | >400 |
| E. cloacae | TN 583 | >400 | >400 | >400 |
| S. marcecens | IFO 12648 | >400 | >400 | >400 |
| S. marcecens | B 315 | >400 | >400 | >400 |
| P. vulgaris | IFO 3988 | >400 | >400 | >400 |
| M. morganii | IFO 3168 | >400 | >400 | >400 |
| P. aeruginosa | IFO 3455 | >400 | >400 | >400 |
| P. aeruginosa | P 9 | >400 | >400 | >400 |
| P. aeruginosa | U 31 | >400 | >400 | >400 |
| P. aeruginosa | GN 3407 | >400 | >400 | >400 |
| P. aeruginosa | B 184 | >400 | >400 | >400 |
| A. calcoaceticus | IFO 13006 | >400 | >400 | >400 |

As shown in Table 4, compounds 1, 2 and 6 did not possess at all antibacterial action against the aerobic bacteria. This suggests that the Compound (I) has a selective antibacterial activity against the genus Campylobacter.

Subsequently, the toxicity of the Compound (I) was investigated. Oral administration of compounds 1 and 6 to mice (200 mg/kg) resulted in no dead animals, thus the Compound (I) is low in toxicity.

As described above, the Compound (I) has a strong antibacterial activity against the genus Campylobacter, e.g. *Campylobacter pylori*; and is of low toxicity. Thus, it can be used for the therapy of infectious diseases due to bacteria belonging to the genus Campylobacter (e.g. diarrhea, food poisoning, etc.) in mammals (e.g. mouse, rat, rabbit, dog, men, etc.). In this case, since the Compound (I) was selectively active against the genus Compylobacter, its administration does not induce the changes in the intestinal flora observed frequently in common antibiotic therapy (e.g. penicillin, cephalosporin, quinolon, etc.). Thus, the treatment with the Compound (I) can not accompany severe risk of undesirable side-effects due to replacement of bacteria (e.g. enteritis, *pseudomembranous colitis*, etc.). Furthermore, since the Compound (I) shows very unique antibacterial spectrum, its mode of action is considered to be different from that of any of the known antibiotics. Thus, the administration of the Compound (I) is unlikely to induce the acquisition of drug resistance of other species of bacteria or the cross-tolerance with other antibiotics.

When the Compound (I) is used as an antibiotic agent for preventing or treating said infectious diseases, it can be administered orally in a dosage form of capsules, tablets, granules, etc. by formulating with a pharmacologically acceptable carriers, such as excipients (e.g. lactose, starch, sucrose, etc.), disintegrators (e.g. starch, carboxymethyl-cellulose calcium, etc.), lubricants (e.g. magnesium stearate, talc, etc.), binders (e.g. hydroxypropyl-cellulose, hydroxypropylmethyl-cellulose, macrogol, etc.), and so on, and it also can be administered parenterally in a dosage form of injectable solutions which desirably have the concentration of the Compound (I) of 0.1 to 20 mg/ml, particularly 2 to 10 mg/ml.

WORKING EXAMPLE

In the following, the present invention is illustrated in a more concrete manner.

EXAMPLE 1

Nonpareils, 1650 g, [sugar core prepared by coating sucrose (75 weight parts) with corn starch (25 weight parts) according to a per se known method, 20–28 mesh] were brought into the CF granulator (CF-360, Freund Industrial Co., Ltd., Japan), and coated, while being sprayed with 1050 ml of a hydroxypropylcellulose solution [2% (w/v)] at 30 ml/min., first with the spraying powder and then with the spraying powder 2, both of which had been prepared by mixing the ingredients listed below, at the rate of 60 g/min. at room temperature with a rotor rotating at 200 rpm, dried in vacuo at 40° C. for 16 hours, and sieved through round sieves, to give spherical granules (14–32 mesh) having a core.

| [spraying powder 1] | |
|---|---|
| compound (1) | 450 g |
| magnesium carbonate | 336 g |
| granulated sugar | 297 g |
| corn starch | 300 g |
| L-HPC | 354 g |
| [degree of substitution with hydroxypropaxyl group: 10.0~13.0% (w/w), mean particle size: not more than 30 μm] | |
| [spraying powder 2] | |
| granulated sugar | 300 g |
| corn starch | 246 g |
| L-HPC (the same one as above) | 246 g |

The granules obtained as above, 3,800 g, were brought into a fluidized-bed coating vessel (Ohkawara Co., Japan), subjected to enteric coating by spraying the enteric coating film solution described below at the rate of 50 ml/min. under the controlled conditions of inlet air at 65° C. and material temperature at 40° C., to give enteric coated spherical granules having a core.

The said granules were mixed with talc and light anhydrous silicic acid, then the mixture was filled into No. 1 hard capsules with a capsule filling machine (Parke-Davis & Co., USA) to give capsules.

| [Enteric coating film solution] | |
|---|---|
| Eudragit L30D-55 | 2,018 g (solid: 605 g) |
| talc | 182 g |
| polyethyleneglycol 6000 | 60 g |
| titanium oxide | 60 g |
| Tween 80 | 27 g |
| water | 4,230 ml |
| [composition in one capsule] | |
| enteric coated granules | 368.8 mg |
| ⎛ compound (1) | 30.0 mg ⎞ |
|   magnesium carbonate | 22.4 mg |
|   Nonpareils | 110.0 mg |
|   granulated sugar | 59.8 mg |
|   corn starch | 36.4 mg |
|   L-HPC | 40.0 mg |
|   hydroxypropylecllulose | 1.4 mg |
|   Eudragit L30D-50 | 44.6 mg |
|   talc | 13.4 mg |
|   polyethyleneglycol 6000 | 4.4 mg |
|   titanium oxide | 4.4 mg |
| ⎝ Tween 80 | 2.0 mg ⎠ |
| talc | 0.6 mg |
| light anhydrous silicic acid | 0.6 mg |
| No. 1 hard capsule | 79.0 mg |
| Total | 449.0 mg |

The dosage of the capsules is, for an adult man, one capsule after each meal per day.

EXAMPLE 2

A 1000 mg quantity of compound (1) was dispersed in distilled water for injection, and 3 ml of 1N-aqueous sodium hydroxide solution was added to dissolve the compound (1), followed by addition of water to make up to the total of 50 ml and sterile filtration by the conventional method. The resulting filtrate was filled in 1 ml portions into vials of a 12 cm$^3$ capacity, followed by lyophilization by means of the conventional technique. The lyophilized powder as contained in vials was dissolved in Solvent A (which was composed of 50 mg of N-methylglucamine, 0.27 ml of 1N-hydrochloric acid and 2 ml of propylene glycol being admixed with ethanol to make up to the total of 4 ml), Solvent B (which was composed of 50 mg of N-methylglucamine, 0.27 ml of 1N-hydrochloric acid, 1.2 ml of polyethylene glycol 400 and 1.2 ml of ethanol being admixed with distilled water for injection to make up to the total of 4 ml), Solvent C (which was composed of 50 mg of N-methylglucamine, 0.27 ml of 1N-hydrochloric acid, 1.2 ml of ethanol and 1.2 ml of propylene glycol being admixed with distilled water for injection to make up to the total of 4 ml) and Solvent D (which was composed of 50 mg of N-methylglucamine, 0.27 ml of 1N-hydrochloric acid and 2.5 ml of polyethylene glycol 400 bing admixed with distilled water for injection to make up to the total of 4 ml), respectively, to perform inspection for their solubilities as well as to conduct investigation into appearance and contents immediately after dissolution and after storage at 25° C. for 24 hours.

The results are shown in Table 5. The lyophilized power showed excellent solubilities in all of these solvents, and were able to be dissolved quickly. In addition to this, the resulting solutions were observed to produce slight changes in appearance immediately after dissolution and after storage for 24 hours, but the changes were found to be so slight that they in no way influence the injectable solution. The solution were found to show no change in the stage of solution while being observed to decrease slightly in content of compound (1).

TABLE 5

Stability of the lyophilized compound (1) after being dissolved in vials:

|  | A | B | C | D |
|---|---|---|---|---|
| Solubility | Good | Good | Good | Good |
| pH after dissolution | 8.7 | 9.0 | 9.0 | 9.0 |
| After dissolution: |  |  |  |  |
| Appearance | Colorless | Colorless | Colorless | Colorless |
| Clarity | Clear | Clear | Clear | Clear |
| Content | 100% | 100% | 100% | 100% |
| After storage at 5° C. for 24 hrs.: |  |  |  |  |
| Appearance | Slightly to lightly green-yellow | | | |
| Clarity | Clear | Clear | Clear | Clear |
| Content* | 97.0% | 96.5% | 96.7% | 96.1% |

Note.
*As measured by use of high-performance liquid chromatography (HPLC), whereby the content determined immediately after preparation was taken as 100.0%.
Chromatographic conditions of HPLC:
Carrier:
Nucleosil 5 C$_{18}$ (supplied by Gas-Chro Kogyo K.K. of Japan) 4.0 mm × 150 mm
Solvent:
Methanol:water:triethylamine (60:40:1, pH 7)
Detection method:
UV spectrophotometry at 285 mm These solutions can use as injections solutions
What is claimed:

1. A method for combatting infectious diseases caused by the genus campylobater which comprises administering to a mammal in need thereof an antibiotially-effective amount of a compound of the formula

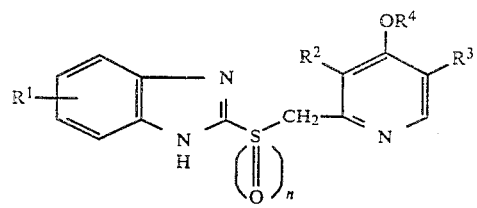

wherein $R^1$ stands for hydrogen, methoxy or triflouromethyl; $R^2$ and $R^3$, being the same or different from each other, stand for hydrogen or methyl; and $R^4$ stands for optionally substituted hydrocarbon residue and n denotes 0 or 1, or a pharmacologically acceptable salt thereof.

2. A method according to claim 1, wherein $R^1$ is hydrogen.
3. A method according to claim 1, wherein $R^3$ is hydrogen.
4. A method according to claim 1, wherein $R^4$ is fluorinated alkyl group.
5. A method according to claim 1, wherein $R^4$ is fluorinated alkyl group.
6. A method according to claim 1, wherein $R^1$ is fluorinated alkyl group.
7. A method according to claim 1, wherein the compound is 2-{3-methyl-4-(2,2,2-trifluoroethoxy)pyrid-2-yl}methylsulfinylbenzimidazole.
8. A method according to claim 1, wherein the compound is 2-{3-methyl-4-(2,2,2-trifluoroethoxy)pyrid-2-yl}methylthiobenzimidazole.
9. A method according to claim 1, wherein the compound is 2-{3-methyl-4-(2,2,3,3,3-pentafluoropropoxy)-pyrid-2-yl}methylsulfinylbenzimidazole.
10. A method according to claim 1, wherein the compound is 2-{3-methyl-4-(2,2,3,3,3-pentafluoropropoxy)-pyrid-2-yl}methylthiobenzimidazole.
11. A method according to claim 1, wherein the compound is 2-{3-methyl-4-(2,2,3,3-tetrafluoropropoxy)pyrid-2-yl}methylsulfinylbenzimidazole.
12. A method according to claim 1, wherein the compound is 2-{3-methyl-4-(2,2,3,3-tetrafluoropropoxy)pyrid-2-yl}methylthiobenzimidazole.
13. A method according to claim 1, wherein the compound is 2-{3-methyl-4-(2,2,3,3,4,4-hexafluorobutyloxy)pyrid-2-yl}methylsulfinylbenzimidazole.
14. A method according to claim 1, wherein the compound is 2-{3-methyl-4-(2,2,3,3,4,4-hexafluorobutyloxy)pyrid-2-yl}methylthiobenzimidazole.
15. A method according to claim 1, wherein the compound is 2-(3,5-dimethyl-4-methoxypyrid-2-yl)methylsulfinyl-5-methoxybenzimidazole.

* * * * *

UNITED STATES PATENT AND TRADEMARK OFFICE
CERTIFICATE OF CORRECTION

PATENT NO. : 5,013,743
DATED : May 7, 1991
INVENTOR(S) : Tomoyuki Iwahi, Hiroshi Satoh It is certified that error appears in the above-indentified patent and that said Letters Patent is hereby corrected as shown below:

Column 8:
In claim 5, line 23, change "1" to --2--.

Signed and Sealed this

Thirteenth Day of December, 1994

Attest:

BRUCE LEHMAN

*Attesting Officer*  *Commissioner of Patents and Trademarks*